United States Patent
Hirota et al.

(10) Patent No.: US 7,491,845 B2
(45) Date of Patent: Feb. 17, 2009

(54) PROCESS FOR PRODUCING ADIPIC ACID

(75) Inventors: Masaji Hirota, Niihama (JP); Koji Hagiya, Ibaraki (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 183 days.

(21) Appl. No.: 11/596,455

(22) PCT Filed: May 18, 2004

(86) PCT No.: PCT/JP2004/007061

§ 371 (c)(1),
(2), (4) Date: Nov. 13, 2006

(87) PCT Pub. No.: WO2005/110962

PCT Pub. Date: Nov. 24, 2005

(65) Prior Publication Data

US 2008/0039653 A1    Feb. 14, 2008

(51) Int. Cl.
*C07C 55/00* (2006.01)
(52) U.S. Cl. .................................................. 562/590
(58) Field of Classification Search ................. None
See application file for complete search history.

(56) References Cited

U.S. PATENT DOCUMENTS 6,344,586 B1    2/2002    Ichihashi et al.

FOREIGN PATENT DOCUMENTS

| CN | 1 401 624 A | 3/2003 |
| JP | 54-135720 | 10/1979 |
| JP | 2841696 | 10/1998 |
| JP | 2003-201265 | 7/2003 |
| JP | 2003-201265 A * | 7/2003 |
| JP | 2003-201266 | 7/2003 |
| JP | 2004-217625 | 8/2004 |

OTHER PUBLICATIONS

Industrial Organic Chemistry—Main Raw Materials and Intermediates—, 1$^{st}$ Edition, supervised a translation by Teruaki Mukaiyama, Tokyo Kagaku Dojin Co., Ltd., Dec. 1978, 14 pgs.

* cited by examiner

*Primary Examiner*—Paul A Zucker
(74) *Attorney, Agent, or Firm*—Foley & Lardner LLP

(57) ABSTRACT

It is provided to a process for producing adipic acid which comprises making a wastewater containing hydroxycaproic acid and discharged from the step of oxidizing cyclohexane with molecular oxygen in a liquid phase react with hydrogen peroxide in the presence of a tungsten catalyst in the pH range of 0 to 6.

4 Claims, No Drawings

PROCESS FOR PRODUCING ADIPIC ACID

TECHNICAL FIELD

The present invention relates to a process for producing adipic acid.

BACKGROUND ART

It has been known that cyclohexane is oxidized to yield a mixture of cyclohexanol and cyclohexanone and the mixture is used as a raw material for producing adipic acid (e.g. supervised a translation by Teruaki Mukaiyama, "Industrial organic chemistry-main raw materials and intermediates-", 1st Edition, TOKYO KAGAKU DOJIN CO., Ltd., December 1978, p. 229-230).

As various oxidation by-products are produced other than desired cyclohexanol and cyclohexanone by oxidizing cyclohexane in a liquid phase, industrially, the reaction is generally carried out so that the conversion rate of cyclohexane may seldom be raised but the selectivity of desired cyclohexanol and cyclohexanone may be raised. Nevertheless, substantial amount of oxidation by-products are produced and therefore, washing the oxidation reaction mixture with water or alkaline water to separate to a mixture containing cyclohexanol, cyclohexanone and cyclohexane and a wastewater containing oxidation by-products is conducted.

Most of oxidation by-products contained in the wastewater discharged by washing are adipic acid and hydroxycaproic acid. Among them, a part or all of adipic acid can be recovered by conducting crystallization treatment of the above-mentioned wastewater, for example, under acidic condition and used efficiently. However, because of poor demand for hydroxycaproic acid as it is, it was usually disposed by incinerating without recovering. As for hydroxycaproic acid, a method for converting hydroxycaproic acid contained in the wastewater to adipic acid by oxidizing the wastewater with oxygen in the presence of platinum group metal catalyst such as palladium is proposed (e.g. JP 2000-103760 A1).

DISCLOSURE OF THE INVENTION

According to the present invention, since a wastewater containing hydroxycaproic acid and discharged from the step of oxidizing cyclohexane with molecular oxygen in a liquid phase can be readily oxidized to convert to adipic acid, carbon source can be efficiently used and waste material can be reduced and load of environment treatment can be reduced. Therefore, it is industrially advantageous.

That is, the present invention is provided to a process for producing adipic acid which comprises making a wastewater containing hydroxycaproic acid and discharged from the step of oxidizing cyclohexane with molecular oxygen in a liquid phase react with hydrogen peroxide in the presence of a tungsten catalyst.

BEST MODE FOR CARRYING OUT THE INVENTION

First, a wastewater containing hydroxycaproic acid and discharged from the step of oxidizing cyclohexane with molecular oxygen in a liquid phase (hereinafter, simply referred to as the wastewater) will be illustrated. The wastewater is a wastewater discharged by oxidizing cyclohexane with molecular oxygen in a liquid phase followed by washing the reaction liquid obtained with water or alkaline water.

The oxidation of cyclohexane in a liquid phase is carried out according to a known method such as Japanese Patent No. 2841696. Generally, it is conducted by blowing molecular oxygen into liquid cyclohexane. As molecular oxygen, oxygen gas may be used and air may be used. A mixed gas of oxygen and an inert gas may be used. The amount of molecular oxygen is not particularly limited and it is usually adjusted so that the conversion of cyclohexane may seldom be raised because of suppressing production of the oxidation by-products as much as possible and improving the selectivity of desired objects.

The oxidation temperature is usually in the range of 80 to 200° C. The reaction pressure may be that to keep the reaction mixture as liquid phase and it is usually in the range of about 100 to 3000 kPa.

The oxidation of cyclohexane in a liquid phase may be carried out in the absence of a catalyst and in the presence of the catalyst. Examples of the catalyst include a salt of cobalt such as cobalt naphthenate and cobalt octanoate; a salt of manganese such as manganese naphthenate and manganese octanoate; and a boric acid compound such as boric acid. In the case of using the catalyst, the amount of the catalyst to be used is usually in the range of 0.001 to 1% by weight relative to 1 part by weight of cyclohexane.

In the reaction liquid obtained by oxidizing cyclohexane with molecular oxygen in a liquid phase, unreacted cyclohexane and various oxidation by-products, and the catalyst and decomposition of the catalyst in the case of using the catalyst, are usually included other than desired cyclohexanol and cyclohexanone. Examples of the oxidation by-products include a carboxylic acid compound such as formic acid, acetic acid, caproic acid, hexanoic acid, oxalic acid, glutaric acid, adipic acid and hydroxycaproic acid; a lactone compound such as e-caprolactone; an ester compound obtained by condensation of the above-mentioned carboxylic acid compound and hydroxycaproic acid; an ester compound obtained by condensation of the above-mentioned carboxylic acid compound and cyclohexanol; and an ester compound obtained by self-condensation of two moleculars of hydroxycaproic acid. The kinds thereof and the amount thereof to be produced are different depending on reaction conditions and usually, adipic acid and hydroxycaproic acid are mostly produced as by-products and they are mainly contained in it.

Since these oxidation by-products represented by hydroxycaproic acid are easy to dissolve in water or alkaline water relatively, oxidation reaction liquid is usually washed with water or alkaline water to separate the wastewater containing oxidation by-products and the mixture containing desired cyclohexanol, desired cyclohexanone and unreacted cyclohexane. The wastewater containing hydroxycaproic acid and discharged by washing is used for the present invention.

The wastewater is usually used as it is for the present reaction. Since adipic acid is also contained in the wastewater in many cases, in those cases, the wastewater after isolating a part or all of adipic acid contained in the wastewater may be used for the present invention. Examples of methods for isolating a part or all of adipic acid from the wastewater include a method comprising crystallizing adipic acid from the wastewater to separate the crystallized adipic acid. Examples of methods comprising crystallizing adipic acid from the wastewater include a method comprising cooling the wastewater and a method comprising concentrating a part of the wastewater.

Next, a process for producing adipic acid by making the wastewater react with hydrogen peroxide in the presence of a tungsten catalyst will be illustrated.

Examples of the tungsten catalyst include tungsten metal or a compound thereof such as tungsten metal, tungsten boride, tungsten carbide, tungsten sulfide, tungsten oxide, tungstic acid and a salt of tungstic acid; and an oxide of tungsten obtained by reacting these tungsten metal or the compounds thereof with hydrogen peroxide. These may be used alone or two or more thereof may be mixed to use. Examples of the salt of tungstic acid include an alkali metal salt of tungstic acid such as sodium tungstate and potassium tungstate; an alkaline earth metal salt of tungstic acid such as calcium tungstate and magnesium tungstate; and ammonium tungstate. Commercial available tungsten metal or the compounds thereof are usually used. When tungstic acid is used as the tungsten catalyst, tungstic acid prepared by neutralizing the salt of tungstic acid such as sodium tungstate with an acid such as sulfuric acid may be used. When the salt of tungstic acid is used as the tungsten catalyst, a salt of tungstic acid prepared by reacting tungstic acid with the corresponding base. Among these tungsten catalysts, tungstic acid, the salt of tungstic acid and tungstic acid prepared by neutralizing the salt of tungstic acid with the acid are preferable.

As hydrogen peroxide used for preparing the oxide of tungsten obtained by reacting tungsten metal or the compounds thereof with hydrogen peroxide, an aqueous hydrogen peroxide solution is usually used. Off course, an organic solvent solution of hydrogen peroxide may be used and the aqueous hydrogen peroxide solution is preferably used in the point of handling easily. The concentration of hydrogen peroxide in the aqueous hydrogen peroxide solution or in the organic solvent solution of hydrogen peroxide is not particularly limited, but in view of volume efficacy and safety, it is practically in the range of about 1 to 60% by weight. As the aqueous hydrogen peroxide solution, a commercially available aqueous hydrogen peroxide solution is usually used as it is, or if necessary, it may be used by appropriately adjusting the concentration by dilution or concentration. In addition, as the organic solvent solution of hydrogen peroxide, a solution prepared by extracting the aqueous hydrogen peroxide solution with the organic solvent or distilling the aqueous hydrogen peroxide solution in the presence of the organic solvent may be used. It is preferred to use tungstens having a smaller particle size in viewpoint of preparing the oxide of tungsten more easily.

The amount of hydrogen peroxide to be used for making react with tungsten metal or the compound thereof is usually 3 moles or more, preferably 5 moles or more relative to 1 mole of tungsten metal or the compound thereof, and the upper limit of the amount is not particularly defined.

The oxide of tungsten is prepared by making tungsten metal or the compound thereof react with hydrogen peroxide. The reaction is usually carried out in an aqueous solution. Off course, the reaction may be carried out in an organic solvent such as an ether solvent such as diethyl ether, methyl tert-butyl ether and tetrahydrofuran; an ester solvent such as ethyl acetate; a tertiary alcohol solvent such as tert-butanol; a nitrile solvent such as acetonitrile and propionitrile; or in a mixture of the organic solvent and water.

The reaction of tungsten metal or the compound thereof with hydrogen peroxide is conducted by mixing both and, in order to increase efficiency of contact between tungsten metal or the compound thereof and hydrogen peroxide, such reaction is preferably conducted with stirring so as to sufficiently disperse tungsten metal or the compound thereof in a solution for preparing the oxide of tungsten. In addition, in viewpoint of increasing efficiency of contact between tungsten metal or the compound thereof and hydrogen peroxide and controlling preparation of the oxide of tungsten more easily, for example, tungstens having a smaller particle size such as a powder are preferably used. The preparing temperature in preparation of the oxide of tungsten is usually about −10 to 100° C.

A homogeneous solution or suspension containing the oxide of tungsten can be prepared by making tungsten metal or the compound thereof react with hydrogen peroxide in water or the organic solvent. The oxide of tungsten may be isolated from the preparation solution by concentration and used for the reaction of the wastewater and hydrogen peroxide and the preparation solution may be used as it is.

Adipic acid can be produced by making the wastewater react with hydrogen peroxide in the presence of the tungsten catalyst. As hydrogen peroxide, an aqueous hydrogen peroxide solution is usually used. Off course, an organic solvent solution of hydrogen peroxide may be used. The concentration of hydrogen peroxide in the aqueous hydrogen peroxide solution or in the organic solvent solution of hydrogen peroxide is not particularly limited, but in view of volume efficacy and safety, it is practically in the range of about 1 to 60% by weight.

Since hydrogen peroxide may be consumed or decomposed by oxidation by-products other than hydroxycaproic acid and the catalyst used in the oxidation of cyclohexane in a liquid phase contained in the wastewater, the amount of hydrogen peroxide to be used may be accordingly decided in consideration of the amount of oxidation by-products other than hydroxycaproic acid and the catalyst contained in the wastewater. The amount of hydrogen peroxide to be used is usually 1.5 moles or more, preferably 2 moles or more per 1 mole of hydroxycaproic acid contained in the wastewater. There is no upper limit of the amount thereof to be used. However, if the amount thereof to be used is too much, it will result in economical disadvantage and therefore, the amount thereof to be used is practically about 10 moles or less, preferably about 5 moles or less.

The amount of the tungsten catalyst is usually about 0.005 to 50 mol %, preferably about 0.01 to 20 mol % as tungsten metal per 1 mole of hydroxycaproic acid contained in the wastewater.

The present reaction is usually conducted by contacting and mixing the tungsten catalyst, the wastewater and hydrogen peroxide. The mixing order of the tungsten catalyst, the wastewater and hydrogen peroxide is not particularly limited and in viewpoint of producing adipic acid in better yield, hydrogen peroxide is preferably added to a mixture of the wastewater and the tungsten catalyst. In this case, hydrogen peroxide is preferably added dropwise thereto. When the oxide of tungsten obtained by making tungsten metal or the compound thereof react with hydrogen peroxide is used, preparation of the oxide of tungsten, which is the catalyst, and reaction of the wastewater and hydrogen peroxide may be performed simultaneously by contacting and mixing tungsten metal or the compound thereof, hydrogen peroxide and the wastewater.

The reaction temperature is usually about 20 to 130° C., preferably about 70 to 110° C. The reaction is usually carried out under an ordinary pressure condition and may be carried out under pressurized or reduced pressure condition.

The reaction of the wastewater and hydrogen peroxide may be carried out in the presence of an organic solvent. Examples of the organic solvent include an ether solvent such as diethyl ether, methyl tert-butyl ether and diglyme; an ester solvent such as ethyl acetate; a tertiary alcohol solvent such as tert-butanol; and a nitrile solvent such as acetonitrile and propionitrile. The amount thereof to be used is not limited.

The present reaction is preferably carried out in the range of pH 0 to 6, more preferably in the range of pH 0 to 4, and furthermore preferably in the range of pH 0 to 2 from the point of the reaction rate. Therefore, when pH of the reaction liquid is out of the above-mentioned range, the reaction is preferably carried out with adjusting pH of the reaction liquid using an acid such as sulfuric acid, hydrochloric acid and nitric acid, or an alkali such as sodium hydroxide.

After completion of the reaction, adipic acid can be isolated by conducting concentration treatment or crystallization treatment of the reaction liquid as it is or after decomposing remained hydrogen peroxide using a reducing agent such as sodium sulfite, if necessary. Adipic acid can be also isolated by adding a water-insoluble solvent to the reaction liquid to conduct extraction treatment and conducting concentration treatment or crystallization treatment of the obtained organic layer.

Depending on the tungsten catalyst used, the tungsten catalyst may exist in the reaction liquid as an insoluble matter. In that case, tungsten metal or the compound thereof used and filtrate containing adipic acid can be separated easily by filtrating in dissolving adipic acid in the reaction liquid and the tungsten catalyst can be recovered as a solid. Adipic acid can be isolated by conducting concentration treatment or crystallization treatment of the obtained filtrate containing adipic acid as it is or after decomposing remained hydrogen peroxide using a reducing agent such as sodium sulfite, if necessary. Adipic acid can be also isolated by adding a water-insoluble solvent to the filtrate to conduct extraction treatment and conducting concentration treatment or crystallization treatment of the obtained organic layer.

Isolated adipic acid may be further purified by a conventional purification method such as recrystallization. The filtrate after isolating adipic acid by conducting crystallization treatment and the water layer after isolating the organic layer by conducting extraction treatment include the tungsten catalyst of the present reaction, and they can be used again for the present reaction as it is or after conducting concentration treatment, if necessary. In the case of isolating the tungsten catalyst as a solid, the solid of the tungsten catalyst isolated can be used again for the present reaction as it is or after conducting washing treatment with water or an organic solvent, if necessary.

EXAMPLES

The present invention will be further illustrated in more detail by Examples. The present invention is not limited to these Examples. High performance liquid chromatography apparatus was used for an analysis. The amount of adipic acid produced in present reaction was calculated by subtracting the amount of adipic acid contained in the wastewater used as law material from the amount of adipic acid contained in the reaction liquid and the yields of adipic acid in the following Examples were calculated based on hyroxycaproic acid in the wastewater.

Example 1

Cyclohexane was oxidized in a liquid phase and the reaction mixture was washed with water to obtain the wastewater containing hydroxycaproic acid together with a mixture of cyclohexanone and cyclohexanol. The wastewater was cooled and the crystallized adipic acid was filtered to obtain the wastewater wherein the content of hydroxycaproic acid was 18.5% by weight. In the wastewater, adipic acid, glutaric acid, ε-caprolactone, esters of adipic acid and esters of hydroxycaproic acid were contained other than hydroxycaproic acid.

Into a 100 mL Schlenk Tube equipped with a reflux condenser, 0.07 g of sodium tungstate, 9.61 g of 30% by weight aqueous hydrogen peroxide and 80 mg of sulfuric acid were charged at room temperature and the mixture was stirred at room temperature for 1 minute to prepare a tungsten catalyst suspension. 14.3 g of the wastewater containing hydroxycaproic acid obtained the above (content of hydroxycaproic acid: 18.5% by weight) was charged into this and the mixture was stirred at an inner temperature of 90° C. for 4 hours to effect reaction. The reaction liquid containing adipic acid was obtained. Yield of adipic acid: 26%.

Example 2

Into a 100 mL Schlenk Tube equipped with a reflux condenser, 0.07 g of sodium tungstate, 1 g of water and 80 mg of sulfuric acid were charged at room temperature and the mixture was stirred at room temperature for 1 minute to prepare the tungsten catalyst suspension. Into the prepared liquid, 14.3 g of the wastewater containing hydroxycaproic acid (content of hydroxycaproic acid: 18.5% by weight) which was as same as that used in the above-mentioned Example 1 was charged. The mixture was adjusted at an inner temperature of 90° C. and then 9.61 g of 30% by weight aqueous hydrogen peroxide was added dropwise thereto over 7 hours. After that, the mixture was stirred at the same temperature for 2 hours to effect reaction and the reaction liquid containing adipic acid was obtained. Yield of adipic acid: 52%.

Example 3

Into a 100 mL Schlenk Tube equipped with a reflux condenser, 0.04 g of sodium tungstate and 1.1 g of 30% by weight aqueous hydrogen peroxide were charged at room temperature and the mixture was stirred at an inner temperature of 50° C. for 15 minutes to prepare the oxide of tungsten. Into the prepared liquid, 8.5 g of 30% by weight of aqueous hydrogen peroxide and 14.3 g of the wastewater containing hydroxycaproic acid (content of hydroxycaproic acid: 18.5% by weight) which was as same as that used in the above-mentioned Example 1 was charged. The mixture was stirred at an inner temperature of 90° C. for 4 hours to effect reaction and the reaction liquid containing adipic acid was obtained. Yield of adipic acid: 26%.

Example 4

Into a 100 mL Schlenk Tube equipped with a reflux condenser, 0.33 g of sodium tungstate, 1 g of water and 0.3 g of sulfuric acid were charged and aqueous tungstic acid solution was prepared. 14.3 g of the wastewater containing hydroxycaproic acid (content of hydroxycaproic acid: 18.5% by weight) which was as same as that used in Example 1 was added thereto and the mixture was adjusted at an inner temperature of 90° C. 9.6 g of 30% by weight aqueous hydrogen peroxide was added dropwise thereto at the same temperature over 10 hours and then the mixture was stirred for 2 hours to effect reaction and the reaction liquid containing adipic acid was obtained. Yield of adipic acid: 80%.

Example 5

Into a 100 mL Schlenk Tube equipped with a reflux condenser, 0.66 g of sodium tungstate, 1 g of water and 0.6 g of sulfuric acid were charged to prepare a tungsten catalyst suspension. 14.3 g of the wastewater containing hydroxycaproic acid (content of hydroxycaproic acid: 18.5% by weight)

which was as same as that used in Example 1 was added thereto and the mixture was adjusted at an inner temperature of 90° C. 9.6 g of 30% by weight aqueous hydrogen peroxide was added dropwise thereto at the same temperature over 7 hours and then the mixture was stirred for 2 hours to effect reaction and the reaction liquid containing adipic acid was obtained. Yield of adipic acid: 86%.

Example 6

Into a 100 mL Schlenk Tube equipped with a reflux condenser, 0.04 g of tungsten metal and 1.1 g of 30% by weight hydrogen peroxide were charged and the mixture was stirred at an inner temperature of 50° C. for 15 minutes to prepare oxide of tungsten. 14.3 g of the wastewater containing hydroxycaproic acid (content of hydroxycaproic acid: 18.5% by weight) which was as same as that used in Example 1 was added thereto and the mixture was adjusted at an inner temperature of 90° C. 8.5 g of 30% by weight aqueous hydrogen peroxide was added dropwise thereto at the same temperature over 7 hours and then the mixture was stirred for 2 hours to effect reaction and the reaction liquid containing adipic acid was obtained. Yield of adipic acid: 35%.

Example 7

Into a 100 mL Schlenk Tube equipped with a reflux condenser, 0.23 g of tungsten oxide, 1 g of water and 0.6 g of sulfuric acid were charged and the mixture was stirred at room temperature for 1 minute. 14.3 g. of the wastewater containing hydroxycaproic acid (content of hydroxycaproic acid: 18.5% by weight) which was as same as that used in Example 1 was added thereto and the mixture was adjusted at an inner temperature of 90° C. 9.61 g of 30% by weight aqueous hydrogen peroxide was added dropwise thereto at the same temperature over 4 hours and then the mixture was stirred for 3 hours to effect reaction and the reaction liquid containing adipic acid was obtained. Yield of adipic acid: 60%.

Example 8

Into a 100 mL Schlenk Tube equipped with a reflux condenser, 0.25 g of tungstic acid, 1 g of water and 0.6 g of sulfuric acid were charged and the mixture was stirred at room temperature for 1 minute. 14.3 g of the wastewater containing hydroxycaproic acid (content of hydroxycaproic acid: 18.5% by weight) which was as same as that used in Example 1 was added thereto and the mixture was adjusted at an inner temperature of 90° C. 9.61 g of 30% by weight aqueous hydrogen peroxide was added dropwise thereto at the same temperature over 4 hours and then the mixture was stirred for 3 hours to effect reaction and the reaction liquid containing adipic acid was obtained. Yield of adipic acid: 62%.

Example 9

Into a 500 mL four-necked flask equipped with a reflux condenser, 4.95 g of sodium tungstate, 15 g of water and 9 g of sulfuric acid were charged to prepare a tungsten catalyst suspension. 214.3 g of the wastewater containing hydroxycaproic acid (content of hydroxycaproic acid: 18.5% by weight) which was as same as that used in Example 1 was added thereto and the mixture was adjusted at an inner temperature of 100° C. 123.6 g of 30% by weight aqueous hydrogen peroxide was added dropwise thereto at the same temperature over 4 hours and then the mixture was stirred for 3 hours to effect reaction and the reaction liquid containing adipic acid was obtained. The reaction liquid was filtered at an inner temperature of 70° C. and a yellow solid was filtered off. The filtrate obtained was cooled to an inner temperature of 10° C. over 12 hours and the crystal of adipic acid precipitated was filtered. Acquisition rate of adipic acid crystal: 59%, yield of adipic acid which is sum of adipic acid containing in crystal and the filtrate: 81%. The above-mentioned yellow solid was washed with water and washed with acetone and dried and analyzed to confirm it was tungstic acid. Content of tungstic acid: 95% by weight.

Example 10

Into a 500 mL four-necked flask equipped with a reflux condenser, 4.4 g of yellow solid of tungstic acid obtained in the above-mentioned Example 9, 0.5 g of sodium tungstate, 15 g of water and 9 g of sulfuric acid were charged to prepare a tungsten catalyst suspension. 214.3 g of the wastewater containing hydroxycaproic acid (content of hydroxycaproic acid: 18.5% by weight) which was as same as that used in Example 1 was added thereto and the mixture was adjusted at an inner temperature of 100° C. 123.6 g of 30% by weight aqueous hydrogen peroxide was added dropwise thereto at the same temperature over 4 hours and then the mixture was stirred for 3 hours to effect reaction and the reaction liquid containing adipic acid was obtained. The reaction liquid was filtered at an inner temperature of 70° C. and a yellow solid was filtered off. The filtrate obtained was cooled to an inner temperature of 10° C. over 12 hours and the crystal of adipic acid precipitated was filtered. Yield of adipic acid combined in crystal and in the filtrate: 68%.

Example 11

Cyclohexane was oxidized in a liquid phase and the reaction mixture was washed with water to obtain the wastewater containing hydroxycaproic acid (content of hydroxycaproic acid: 8.8% by weight) together with a mixture of cyclohexanone and cyclohexanol. In the wastewater, adipic acid, glutaric acid, e-caprolactone, esters of adipic acid and esters of hydroxycaproic acid were contained other than hydroxycaproic acid.

Into a 500 mL four-necked flask equipped with a reflux condenser, 2.47 g of sodium tungstate, 7.5 g of water and 9.0 g of sulfuric acid were charged at room temperature to prepare a tungsten catalyst suspension. 226.6 g of the above-mentioned wastewater containing hydroxycaproic acid (content of hydroxycaproic acid: 8.8% by weight) was added thereto and the mixture was adjusted at an inner temperature of 100° C. 72.1 g of 30% by weight aqueous hydrogen peroxide was added dropwise thereto at the same temperature over 8 hours and then the mixture was stirred for 3 hours to effect reaction and the reaction liquid containing adipic acid was obtained. The reaction liquid was filtered at an inner temperature of 70° C. and a yellow solid was filtered off. The filtrate obtained was cooled to an inner temperature of 10° C. over 12 hours and the crystal of adipic acid precipitated was filtered. Yield of adipic acid combined in crystal and in the filtrate: 89%.

Example 12

Into a 500 mL four-necked flask equipped with a reflux condenser, 2.47 g of sodium tungstate, 7.5 g of water and 9.0 g of sulfuric acid were charged at room temperature to prepare a tungsten catalyst suspension. 233.2 g of the wastewater containing hydroxycaproic acid (content of hydroxycaproic acid: 8.8% by weight) which was as same as that used in Example 11 was added thereto and the mixture was adjusted at an inner temperature of 100° C. 432.4 g of 5% by weight aqueous hydrogen peroxide was added dropwise thereto at the same temperature over 10 hours and then the mixture was stirred for 3 hours to effect reaction and the reaction liquid containing adipic acid was obtained. The reaction liquid was filtered at an inner temperature of 70° C. and a yellow solid was filtered off. The filtrate obtained was cooled to an inner temperature of 10° C. over 12 hours and the crystal of adipic acid precipitated was filtered. Yield of adipic acid combined in crystal and in the filtrate: 95%.

Example 13

Cyclohexane was oxidized in a liquid phase and the reaction mixture was washed with water to obtain the wastewater containing hydroxycaproic acid (content of hydroxycaproic acid: 7.5% by weight) together with a mixture of cyclohexanone and cyclohexanol. In the wastewater, adipic acid, glutaric acid, e-caprolactone, esters of adipic acid and esters of hydroxycaproic acid were contained other than hydroxycaproic acid.

Into a 300 mL four-necked flask equipped with a reflux condenser, 1.29 g of sodium tungstate, 3.9 g of water and 6.8 g of 60% nitric acid were charged at room temperature to prepare a tungsten catalyst suspension. 120 g of the above-mentioned wastewater containing hydroxycaproic acid (content of hydroxycaproic acid: 7.5% by weight) was added thereto and the mixture was adjusted at an inner temperature of 100° C. 37.6 g of 30% by weight aqueous hydrogen peroxide was added dropwise thereto at the same temperature over 6 hours and then the mixture was stirred for 4 hours to effect reaction and the reaction liquid containing adipic acid was obtained. Yield of adipic acid: 73%.

Example 14

Into a 300 mL four-necked flask equipped with a reflux condenser, 2.6 g of sodium tungstate, 30 g of water and 6.8 g of 60% nitric acid were charged at room temperature to prepare a tungsten catalyst suspension. 120 g of the wastewater containing hydroxycaproic acid (content of hydroxycaproic acid: 7.5% by weight) which was as same as that used in Example 13 was added thereto and the mixture was adjusted at an inner temperature of 80° C. 32.9 g of 30% by weight aqueous hydrogen peroxide was added dropwise thereto at the same temperature over 6 hours and then the mixture was stirred for 4 hours to effect reaction and the reaction liquid containing adipic acid was obtained. Yield of adipic acid: 84%.

The invention claimed is:

1. A process for producing adipic acid which comprises making a wastewater containing hydroxycaproic acid and discharged from the step of oxidizing cyclohexane with molecular oxygen in a liquid phase react with hydrogen peroxide in the presence of a tungsten catalyst in the pH range of 0 to 6, wherein hydrogen peroxide is added dropwise to a mixture of the tungsten catalyst and the wastewater containing hydroxycaproic acid.

2. The process for producing adipic acid according to claim 1, wherein the tungsten catalyst is an oxide of tungsten obtained by reacting at least one tungsten metal or a compound thereof selected from tungsten metal, tungsten boride, tungsten carbide, tungsten sulfide, tungsten oxide, tungstic acid and a salt of tungstic acid with hydrogen peroxide.

3. The process for producing adipic acid according to claim 1, wherein the wastewater containing hydroxycaproic acid is a wastewater containing hydroxycaproic acid and adipic acid mainly.

4. The process for producing adipic acid according to claim 1, wherein the wastewater containing hydroxycaproic acid is a wastewater obtained by removing a part or all of adipic acid contained in the wastewater.

* * * * *